United States Patent [19]

Haase et al.

[11] Patent Number: 5,741,783
[45] Date of Patent: Apr. 21, 1998

[54] N-CYANOMETHYLATED CHITOSANS AND HYDROLYSATES THEREOF

[75] Inventors: Jürg Haase, Bettingen; Martin Kuhn, Dornach, both of Switzerland

[73] Assignee: Ciba Specialty Chemicals Corporation, Tarrytown, N.Y.

[21] Appl. No.: 576,628

[22] Filed: Dec. 21, 1995

[30] Foreign Application Priority Data

Dec. 22, 1994 [CH] Switzerland .................. 03 899/94

[51] Int. Cl.⁶ .................. A61K 31/73; C08B 37/08
[52] U.S. Cl. .................. 514/55; 514/55; 514/847; 536/20; 536/124; 424/401
[58] Field of Search .................. 514/55, 847; 536/20, 536/124; 424/401

[56] References Cited

U.S. PATENT DOCUMENTS

| | | | |
|---|---|---|---|
| 2,010,176 | 8/1935 | Brodersen | 8/127 |
| 2,855,428 | 10/1958 | Singer et al. | 558/346 |
| 5,442,048 | 8/1995 | Meister et al. | 536/20 |

FOREIGN PATENT DOCUMENTS

| | | |
|---|---|---|
| 0274350 | 7/1988 | European Pat. Off. . |
| 0354344 | 2/1990 | European Pat. Off. . |
| 2523962 | 9/1983 | France . |
| 2105557 | 8/1972 | Germany . |
| 9222698 | 12/1992 | WIPO . |

OTHER PUBLICATIONS

Muzzarelli et al., Carbohydrate Research, 107 (1982), pp. 199–214.
Derwent Abstracts, AN 94–032044, JP 5339598A Dec. 21, 1993.
Derwent Abstracts, AN 84–229987, SU 1067109A Jan. 15, 1984.
Carbohydrate Polymers 24(3), (1994), pp. 209–214.
Carbohydrate Polymers 8(1) (1988), pp. 1–21.

*Primary Examiner*—Kathleen K. Fonda
*Attorney, Agent, or Firm*—Kevin T. Mansfield

[57] ABSTRACT

The invention relates to N-cyanomethylated chitosans of formula (1) and to the hydrolysates thereof of formula (2), as well as to processes for the preparation of these compounds. The cyanomethylated chitosans, in particular the hydrolysates corresponding to formula (2), find versatile utility as separating membranes, complexing agents, encrustation inhibitors, stabilisers for bleaching liquors, moisture retainers in cosmetic compositions, thickeners and repellents.

6 Claims, No Drawings

N-CYANOMETHYLATED CHITOSANS AND HYDROLYSATES THEREOF

The present invention relates to N-cyanomethylated chitosans, to the preparation thereof, to the use of these compounds as separating membranes, to the hydrolysates of said N-cyanomethylated chitosans, to the use of these hydrolysed compounds as thickeners, repellants, sequestrants, complexing agents, encrustation inhibitors, stabilisers for bleaching liquors and as moisture retainers in cosmetic compositions.

The N-cyanomethylated chitosans of this invention contain repeating units of formula

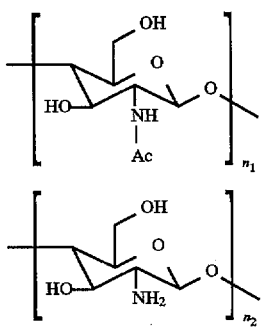
(1)

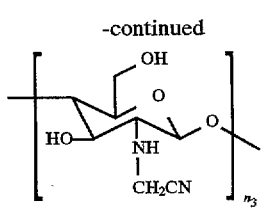

wherein $n_1$ is 0 to 0.6, preferably 0.05 to 0.20;

$n_2$ is 0 to 0.20, preferably 0.05 to 0.10;

$(n_3+n_4)$ is 0.4 to 1.0, preferably 0.8 to 0.95.

The N-cyanomethylated chitosans of this invention are derived from chitosan, which is obtained by deacetylation of chitin, a naturally occurring poly-(N-acetylglucosamine). Also comprised are chitosans which are degraded in the chitin deacetylation processes to oligomeric fragments.

Chitosan is insoluble in neutral and alkaline medium. However, owing to its chemical structure it forms in acid medium soluble salts with specific organic and inorganic acids.

The preparation of the N-cyanomethylated chitosans of this invention is carried out in the practice of this invention in a reaction analogous to the Strecker synthesis by reaction of chitosan with formaldehyde and hydrogen cyanide. The entire reaction course, including the chitin deacetylation, can be illustrated as follows:

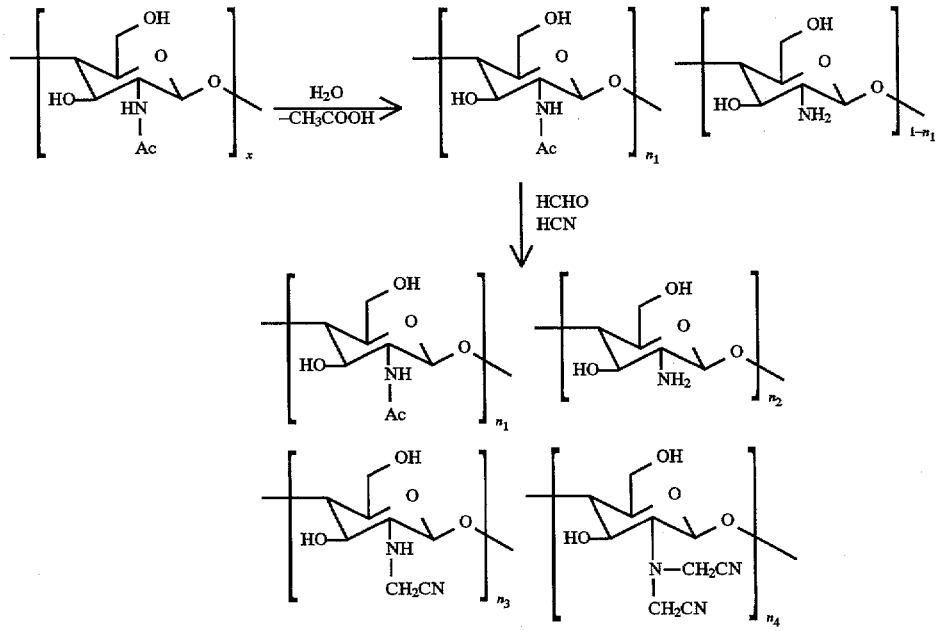

wherein x is 5 to 10000, preferably 20 to 500;

$n_1$ is 0 to 0.6 preferably 0.05 to 0.2 part, based on x;

$n_2$ is 0 to 0.2, preferably 0.05 to 0.1 part, based on x;

$(n_3+n_4)$ is 0.4 to 1.0, preferably 0.8 to 0.95 part, based on x.

The reaction can be carried out with particular advantage in the temperature range from 10° to 70° C., preferably using formic acid as solvent. It is preferably proceeded in the manner that a water soluble salt of hydrogen cyanide, preferably NaCN, is yielded in the formic acid solution of the chitosan and adding at the same temperature the first half of the formaldehyde, preferably as 37% by weight solution of formaline or paraformaldehyde. The temperature is raised up to 70° C., then the second half of the formaldehyde is added.

The reaction times are from 0.5 to 12 hours, preferably from 2 to 5 hours. The product solution is then charged into a sufficient amount of water. The polymeric nitrile is practically completely water insoluble from a substitution degree of 50% and can be isolated quantitatively as blue-grey, gum-like, viscous mass, for example by washing the precipitated polymer with deionised water. The polymeric material is usually crushed in a mixer in the presence of water, the suspension is neutralised with NaOH, the material isolated by suction filtration, after washed and air-dried (=moist product).

The reaction temperature and reaction time have a considerable influence on the degree of methylation of the N-cyanomethylation. The reaction is preferably carried out using formic acid as solvent.

The preparation of the N-cyanomethylated chitosans of this invention is a further object of the invention.

The chitosan derivatives of this invention are polymers having film-forming properties. They form tough, mechanically and chemically resistant films from a solution containing formic acid. They are therefore particularly useful for the preparation of separating membranes of superior strength.

The hydrolysates of the N-cyanomethylated chitosans of this invention constitute yet a further object of the present invention. They contain repeating units of formula

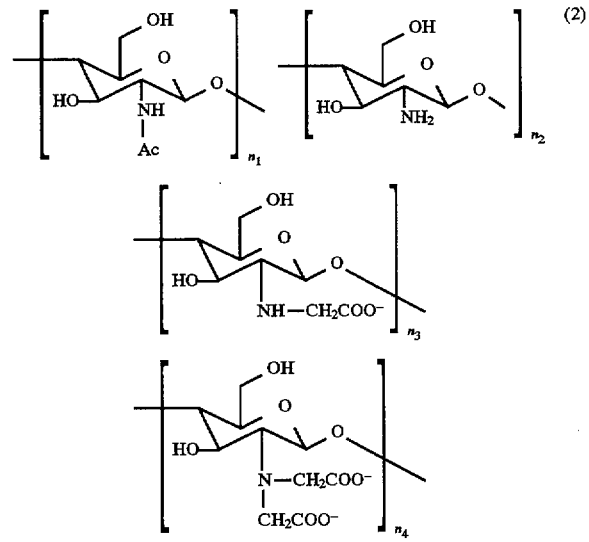

wherein $n_1$ is 0 is 0.6, preferably 0.05 to 0.20;

$n_2$ is 0.01 to 0.20, preferably 0.05 to 0.10;

$(n_3+n_4)$ is 0.4 to 1.0, preferably 0.8 to 0.95;

The preparation of the hydrolysates of this invention from the corresponding N-cyanomethylated compounds is carried out in accordance with the following reaction scheme:

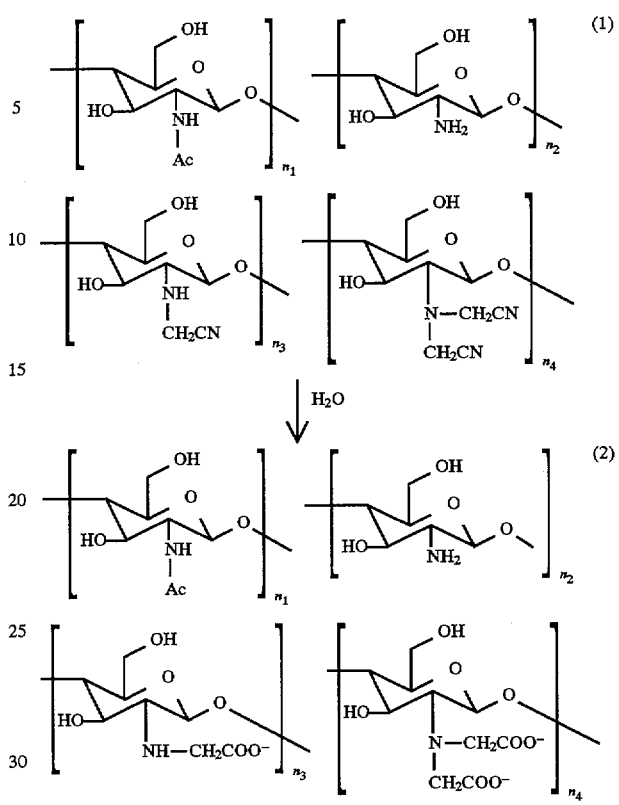

wherein $n_1$ is 0 to 0.6, preferably 0.05 to 0.20;

$n_2$ is 0.01 to 0.20, preferably 0.05 to 0.10;

$(n_3+n_4)$ is 0.4 to 1.0, preferably 0. to 0.95.

The process for the preparation of the hydrolysed N-cyanomethylated chitosans is a further object of the invention.

For hydrolysis the moist product prepared above is suspended in diluted c. 1.5% NaOH and overboiled at c. 80° C. for c. 50 hours. Bright-yellow, aqueous solutions are formed, which are clarified form impurities in the usual manner. After drying and crushing in a mixer a bright-yellow powder is obtained.

The hydrolysed N-cyanomethylated chitosans of formula (2) have sequestrating properties. Owing to their pronounced sequestrating action for heavy metal ions even at low concentrations, it is possible to use the hydrolysed products for removing such cations from contaminated water, typically for removing iron or copper ions from mains water. They may also be used as additives in numerous textile finishing processes. Alone or in combination with cationic, anionic or neutral detergents they can be used as additives in detergent formulations. To be singled out for special mention in this connection is their activity as water softeners and encrustation inhibitors. The invention therefore also relates to the use of the N-cyanomethylated chitosans of this invention for preventing the adherence to, or formation of, solid deposits on inorganic or organic substrates. The substrates may typically be glass, ceramics, metals and metal alloys, natural or synthetic plastics, paper, textiles, leather, or plant or animal organs or tissues.

The hydrolysates of the N-cyanomethylated chitosans of this invention have a surprisingly good capacity for complexing metal ions, in particular alkaline earth metal ions, whereby the precipitation of polymeric metal salts, especially in the case of polyvalent cations, can be favourably influenced or prevented. They are therefore also suitable as additives in detergent formulations, as they enhance the detergent power and prevent soil redeposition on the washed fabric. Furthermore, they act as crystallisation inhibitors, especially in the formation of alkaline earth metal carbonates in the washing process and so influence the growth and morphology of the resultant crystals and their size distributions, as well as on the aggregation and adhesion properties. They are therefore suitable for use as scale inhibitors for water treatment to prevent the formation of deposits in water-conducting systems, as for example water treatment plants, conduits and on the heating coils of steam generators. In the cosmetic sector they may be used, inter alia, as additives in dental care products for inhibiting the formation of dental plaque. They can also be used for the treatment of textiles, for example cotton.

The hydrolysed N-cyanomethylated chitosans of this invention further find utility as bleaching stabilisers, typically in detergent compositions, or in the bleaching of textiles, cellulose or paper stock. In this utility, the chelating agents bind the calcium, magnesium, iron, copper or manganese ions present in the bleaching liquors and simultaneously prevent the precipitation of alkaline earth metal carbonate or hydroxide and the decomposition of the per compound.

A further object of the invention is therefore the application process for bleaching cellulosic fibre materials. The process comprises treating the fibre material with an aqueous liquor which contains at least one N-cyanomethylated chitosan of this invention, an alkali metal hydroxide, a water-soluble magnesium salt and a per compound.

The per compound may suitably be selected from the group consisting of alkali metal peroxodisulfates, preferred compounds being potassium and, more particularly, sodium peroxodisulfate. Sodium peroxodisulfate ($Na_2S_2O_8$), which is normally used as a solid, is very particularly preferred. The preferred per compound is hydrogen peroxide which, owing to its superior stability, is normally used as a concentrated solution of c. 30–60% by weight.

Particularly suitable alkali metal hydroxides are potassium or, preferably, sodium hydroxide, preferably in the form of a concentrated solution of c. 30% by weight, or as solid potassium or, preferably, sodium hydroxide.

In addition to comprising the novel formulation, alkali metal hydroxide and a per compound, the bleaching liquors may also comprise an optional component selected from the group consisting of wetting agents or surfactants, antifoams or deaerators and/or fluorescent whitening agents.

The application process for bleaching cellulosic fibre materials using the novel bleach composition is carried out by per se known methods.

The cellulosic fibre material to be treated may be in any form of presentation, typically as loose material, yarn, woven or knitted goods. It will normally always consist of textile fabrics that are made from pure textile cellulose fibres or from blends of textile cellulose fibres with synthetic textile fibres.

The hydrolysed N-cyanomethylated chitosans of this invention further in the form of their salts, in particular of their alkaline earth metal and ammonium salts, are extremely hygroscopic and, owing to their hydropectic action, are suitable for use as moisture retainers for the skin or mucous membranes in cosmetic formulations, typically in skin- and hair-care products and deodorants. The hydrolysed N-cyanomethylated chitosans of this invention are able to bind iron ions on the skin and can therefore replace the EDTA conventionally used in creams, in particular sun creams.

Hence another object of the invention is a cosmetic composition comprising at least one hydrolysed N-cyanomethylated compound containing repeating units of formula (2) of this invention as well as cosmetically acceptable carriers or adjuvants.

The cosmetic composition of this invention further comprises 0.1 to 15% by weight, preferably 0.2 to 10% by weight, based on the total weight of said composition, of a hydrolysed N-cyanomethylated compound of this invention further that contains repeating units of formula (2) as well as cosmetically acceptable carriers or adjuvants.

The cosmetic composition can be prepared by physically mixing a hydrolysed N-cyanomethylated compound that contains repeating units of formula (2) of this invention with the adjuvants by conventional methods, typically by simple stirring of the single components.

The novel cosmetic composition can be formulated as water-in-oil or oil-in-water emulsion, as oil-in-oil alcoholic solution, as vesicular dispersion of an ionic or nonionic amphiphilic lipid, as gel, solid stick or as aerosol formulation.

Any conventional emulsifier can be used for the novel cosmetic compositions, conveniently one or more than one ethoxylated ester of natural derivatives, for example polyethoxylated esters of hydrogenated castor oil; or a silicone oil emulsifier such as silicone polyol; a fatty acid or ethoxylated fatty acid soap; an ethoxylated fatty alcohol; a sorbitan ester or ethoxylated sorbitan ester; an ethoxylated fatty acid; or an ethoxylated glyceride.

The cosmetic formulation may also comprise further components such as emollients, emulsion stabilisers, suntan promoters, moisture retainers such as glycerol, preservatives, perfumes and colorants.

The hydrolysed N-cyanomethylated chitosans of this invention also have a viscosity increasing and dispersing action in aqueous solutions. They are thus suitable for use as additives in suspensions, emulsions and aqueous solutions, for example in the manufacture of foodstuffs or active substance concentrates as well as in dye and pigment formulations.

The hydrolysed N-cyanomethylated chitosans of this invention can also have biocidal activity, typically bacteriostatic, fungistatic or algicidic activity.

Furthermore, the hydrolysed N-cyanomethylated chitosans of this invention can be used as repellants.

In the following Examples parts and percentages are by weight.

Preparation of the novel N-cyanomethylated chitosans

EXAMPLE 1

20.0 g of chitosan (Fluka Nr. 2271, low molecular, average molecular weight c. 70 000) having a moisture content of 9.24%, an amine value of 4.78/4.79 meq/g, and comprising, calculated therefrom, 11.86 mol % of N-acetyl-D-glucopyranosamine and 88.14 mol % of D-glucopyranosamine units, and having an average mmolar mass of 166.16 and for which the analytical data are as follows:

|  | C | H | N | $H_2O$ | ΔO |
|---|---|---|---|---|---|
| found | 40.7 | 7.3 | 7.5 | 9.24 | 35.26 |
| found, based on anhydrous product | 44.8 | 6.91 | 8.26 |  | 39.99 |
| calculated | 45.09 | 6.82 | 8.43 |  | 39.66 | corresponding to 18.15 g of chitosan 100% (0.1092 mol), are dissolved in 400 ml of techn. formic acid (85%) in a 800 ml flask with ground glass stopper and fitted with anchor stirrer, thermometer, reflux condenser with sealing liquid feed and powder metering feed. To the almost clear solution (undissolved fraction<0.5%) of the polyaminopolysaccharide are then slowly added at 15° C. from the dropping funnel 12.5 g (0.25 mol) of techn. NaCN (98%) and the mixture is slowly stirred for 3 hours. At the same temperature, 20.5 g of 37% formalin (7.6 g of $CH_2O$=0.253 mol), diluted with deionised water to 130 ml, are added dropwise over a period of 1.5 hours. Stirring is then continued for 24 hours at room temperature. The deep blue, high-viscosity solution is charged into 3 liters of deionised water, whereupon the reaction mass solidifies after some time. The precipitation bath is replaced with fresh water and the coarsely precipitated material is crushed in a mixer. The resultant suspension is filtered with suction, the filter product is washed with 3 liters of deionised water, and afterwards dried at 50° C./15 mbar for 48 hours, giving 26.4 g of a hard, greenish blue, brittle material for which the following analytical data are obtained:

|  | C | H | N | $H_2O$ | AO |
|---|---|---|---|---|---|
| found | 48.6 | 5.3 | 14.2 | 0.31[1] | 31.59 |
| found, based on anhydrous product | 48.7 | 5.28 | 14.24 g |  | 31.73 |

[1]expelled at 130° C.

The degree of substitution DS calculated from the analytical data is 0.725. The analytical data calculated therefrom are:

|  | C | H | N | O |
|---|---|---|---|---|
| calculated | 48.49 | 5.94 | 13.93 | 31.63 |

The N-cyanomethylated polyaminopolysaccharide is soluble in DMSO and concentrated formic acid. The IR-spectrum confirms the structure (absorption band at 2249 $cm^{-1}$ for —N—$CH_2CN$; bands at 1673 $cm^{-1}$ and 1553 $cm^{-1}$ for the N-acetyl group).

EXAMPLE 2

A laboratory paddle drier having a volume of 1000 ml and equipped with 2 feed inlets and temperature control is charged with 800 ml of techn. formic acid (85%). Then 40 g of the chitosan described in Example 1 are gradually added, with stirring. The mixture is thereafter stirred for 15 hours at room temperature until the material is almost completely dissolved. After reaching a thermostatically controlled temperature of 15° C., 18.5 g of technical NaCN (98%) (98%; =36.26 g; 100%=0.74 mol) are slowly added simultaneously from each of the two feed inlets. The reaction mixture is afterwards stirred for 3 hours at 15° C., then warmed to room temperature. Then a solution of 40.5 g of formalin 37% (=15 g $CH_2O$=0.5 mol), bulked with distilled water to a total volume of 100 ml, and apportioned equally among 2 dropping funnels, is added very slowly, with efficient stirring. After addition of 30 ml of the formalin solution from each dropping funnel, the temperature is raised via the temperature control to 40° C. and, at this temperature, the remainder of the formalin solution is added dropwise, followed by stirring for 20 hours at 40° C. The resultant high-viscosity, deep greenish-blue N-cyanomethylated polyaminopolysaccharide is charged direct into five liters of deionised water in which the reaction product gradually solidifies to a greenish-blue product. The precipitation bath is decanted and the polymer is taken up in fresh water and crushed in a mixer. The resultant suspension is stirred for 24 hours to remove included salts, the aqueous phase is then adjusted with 30% NaOH to pH 7.5, whereupon the reaction product undergoes a colour change (from greenish-blue to dark yellow). The suspension is filtered with suction, and the filter product is washed with 5 liters of deionised water.

Yield (moist): 469.7 g.

29.9 g of the moist crude product are dried at 50° C./15 mbar for 48 hours and yield 3.3 g of a yellowish light brown, hard, brittle product for which the following analytical data are obtained:

|  | C | H | N | $H_2O$ | AO |
|---|---|---|---|---|---|
| found | 47.7 | 5.6 | 14.3 | 0.83*) | 31.57 |
| found, based on anhydrous product | 48.1 | 5.56 | 14.42 |  | 31.92 |

*)expelled at 150° C.

The degree of substitution DS calculated from the analytical data is 0.745. The analytical data calculated therefrom are:

|  | C | H | N | O |
|---|---|---|---|---|
| calculated | 48.59 | 5.92 | 14.10 | 31.41 |

The product is soluble in DMSO and conc. formic acid. The IR-spectrum confirms the structure (absorption band at 2249 $cm^{-1}$ for —N—$CH_2CN$, bands at 1673 $cm^{-1}$ for the N-acetyl group).

EXAMPLE 3

20 g of the chitosan described in Example 1 are dissolved in a 800 ml flask with ground glass stopper and fitted with anchor stirrer, thermometer, reflux condenser with sealing liquid feed and powder metering funnel in 400 ml of techn. formic acid (85%). To the almost clear solution (undissolved fraction<0.5%) of the polyaminopolysaccharide are then slowly added, at room temperature, 22.2 g of formalin 37% (=8.2 g $CH_2O$=0.273 mol) and the mixture is slowly stirred for 30 minutes. A solution of 6.4 g (0.128 mol) of techn. NaCN (98%) in 20 ml of distilled water is then added dropwise, within 1.5 hours also at room temperature. Stirring is continued for 5 hours, the temperature is raised to 50° C. and again a solution of 7.7 g (0.154 mol) of techn. NaCN (98%) in 30 ml of distilled water is added dropwise. Stirring is continued for 24 hours at 50° C. and for 3 hours at 60° C. and the dark greenish-blue, high-viscosity solution is charged to 3 liters of deionised water, whereupon the reaction mass gradually solidifies. The precipitation bath is decanted and the solid is taken up in fresh water. The polymer is crushed in a mixer and the resultant suspension is adjusted with 30% NaOH to pH 7.5. The suspension is filtered with suction, affording 174.4 g of moist filter product of which 43.6 g are dried in a drying oven at 50° C./15 mbar for 12 hours. Yield: 6.4 g of a pale yellowish brown, hard, brittle product for which the following analytical data are obtained:

|  | C | H | N | $H_2O$ | AO |
|---|---|---|---|---|---|
| found | 46.9 | 5.6 | 12.7 | 1.94*) | 32.86 |
| found, based on anhydrous product | 47.83 | 5.49 | 12.95 |  | 33.73 |

*)determined by expelling at 130° C.

The degree of substitution DS calculated from the analytical data is 0.565. The analytical data calculated therefrom are:

|  | C | H | N | O |
| --- | --- | --- | --- | --- |
| calculated | 47.74 | 6.14 | 12.72 | 33.40 |

The product is soluble in conc. formic acid. The IR-spectrum is qualitatively in accord with the IR spectra of Examples 1 and 2. Molar mass: 198.4.

EXAMPLE 4

130 g of the moist product obtained in Example 3 (c. 8.7 g dry weight=0.0934 mol) are weighed into a 800 ml flask with ground glass stopper and fitted with anchor stirrer, thermometer and reflux condenser, and then 200 ml of deionised water and 120 ml of 1N NaOH are added. The mixture is stirred for 48 hours at a bath temperature of 100° C. The presence of gaseous ammonia is detected with pH paper. The batch is charged to 2 liters of deionised water and the yellowish-brown solution that contains after several hours minor amounts of gel is clarified over 140 S filter gauze. The filtrate, which is concentrated under reduced pressure (30 mbar/50° C.) to a volume of c. 100 ml (highly viscous clear solution), is precipitated in 3 liters of EtOH$_{abs}$, and the precipitated polyaminopolycarboxylic acid Na-salt is isolated by suction filtration and dried at 50° C./0.5 mbar for 48 hours.

Yield: 21.8 g.

Filter residue: 2.8 g (c. 8%).

The product gives a clear solution in water of pH 10.

Amine value: 3.64/3.70 meq/g (determined by back titration with 0.1N NaOH after addition of an excess of hydrochloric acid; titration time: 1.5 hours).

Sum of amine value+carboxy value: 6.06/6,16 meq/g (determined by titration with 0.1N HClO$_4$ in H$_2$O/glacial acetic acid 1:30; after stirring for 2 and 16 hours respectively).

Carboxy value: 2.44 meq/g (from difference)

The product is extremely hygroscopic.

Solubility as function of the pH

| Concentration [g/l] | Onset of precipitation (at pH) |
| --- | --- |
| 9.13 | 5.2 |
| 4.28 | 4.3 |
| 1.06 | 3.2 |

The resultant polyaminopolycarboxylic acid can thus be precipitated and separated as internal salt.

$Ca^{2+}$ sequestering capacity: 102 mg $Ca^{2+}$/g

IR spectrum: nitrile bands and bands for N-acetyl group have disappeared.

EXAMPLES 5 to 11

In these Examples different chitosans are used in different concentrations and varying the ratio hydrogen cyanide/formaldehyde. The chitosans used in the Examples (C1–C4) are listed in the Table 1:

TABLE 1

| | | | | | | | Chitosans used | | | |
| --- | --- | --- | --- | --- | --- | --- | --- | --- | --- | --- |
| | (Chitin)$_x$ | (Chitosan)$_y$ | H$_2$O- | Amine | Deacet.- | | Elemental analysis[2] | | | |
| | x [mol %] | x [mol %] | content [%][3] | numcalc [mEg/g][4] | degree [mol %] | MG [Da] | C$_{calc}$/ C$_{found}$ | H$_{calc}$/ H$_{found}$ | N$_{calc}$/ N$_{found}$ | O$_{calc}$/ O$_{found}$ |
| C1 | 0.1231 | 0.8769 | 9.24 | 5.2720 | 87.69 | 166.355 | 45.10/ 44.84 | 6.82 6.91 | 8.42 8.26 | 39.66 39.66 |
| C2 | 0.1333 | 0.8667 | 11.20 | 5.1971 | 86.67 | 166.765 | 45.13/ 45.12 | 6.81 6.75 | 8.40 8.13 | 39.66 40.00 |
| C3 | 0.1383 | 0.8617 | 11.45 | 5.1609 | 86.17 | 166.974 | 45.15/ 45.25 | 6.81 6.84 | 8.39 8.20 | 39.65 39.71 |
| C4 | 0.0930 | 0.9070 | 7.42 | 5.4946 | 90.70 | 165.071 | 45.01/ 44.93 | 6.83 6.91 | 8.49 8.40 | 39.67 39.76 |

[2]calculated for water-free product based on the amine number;
[3]determined by expelling at 130° C.
[4]mixed with exactly 0.5 ml of 0.1 N HCl + 3 ml dest. water; titrated after 4 days with 0.1 N NaOH Table 2a shows the reaction conditions and the composition of the obtained chitosan-N-acetic acid nitriles.

TABLE 2a

| Ex. | Chitosan used | weight [g][5] | solvent [ml] [%] | NaCN/ CH$_2$O | (Chitin)$_x$ | (Chitosan)$_y$ | (Chitosan-DN)$_z$[6] | DS (%) | yield (g)[7] | content FW (%) | MG (Da) |
| --- | --- | --- | --- | --- | --- | --- | --- | --- | --- | --- | --- |
| 5 | C1 | 40.0 | 800 85 | 0.7399/ 0.5015 | 0.1231 | 0.2069 | 0.6700 | 76.4 | 407.90 | 12.71 | 218.6 |
| 6 | C1 | 40.0 | 900 | 0.7399/ | 0.1231 | 0.2693 | 0.6076 | 69.3 | 511.64 | 10.52 | 213.8 |

TABLE 2a-continued

| Ex. | Chito-san used | weight [g][5] | sol-vent [ml] [%] | NaCN/ $CH_2O$ | (Chi-tin)$_x$ | (Chito-san)$_y$ | (Chito-san-DN)$_z$[6] | DS (%) | yield (g)[7] | content FW (%) | MG (Da) |
|---|---|---|---|---|---|---|---|---|---|---|---|
|  |  |  | 98 | 0.5015 |  |  |  |  |  |  |  |
| 7 | C2 | 40.0 | 800 | 0.7399/ | 0.1333 | 0.2646 | 0.6021 | 69.5 | 522.16 | 9.58 | 213.8 |
|  |  |  | 85 | 0.5015 |  |  |  |  |  |  |  |
| 8 | C3 | 36.6 | 500 | 0.4295/ | 0.1383 | 0.3613 | 0.5000 | 58.0 | 49.57 | 97.92 | 206.0 |
|  |  |  | 98 | 0.4302[8] |  |  |  |  |  |  |  |
| 9 | C4 | 43.2 | 1100 | 0.7320/ | 0.0930 | 0.3000 | 0.6070 | 66.9 | 505.2 | 12.90 | 212.5 |
|  |  |  | 85 | 0.6000 |  |  |  |  |  |  |  |
| 10 | C4 | 43.2 | 1200 | 0.7320/ | 0.0930 | 0.2770 | 0.6300 | 69.5 | 415.8 | 14.51 | 214.3 |
|  |  |  | 85 | 0.6000 |  |  |  |  |  |  |  |
| 11 | C4 | 43.2 | 1200 | 0.7320/ | 0.0930 | 0.2700 | 0.6370 | 70.2 | 474.2 | 13.17 | 214.8 |
|  |  |  | 85 | 0.6100 |  |  |  |  |  |  |  |

[5]tel quel
[6]Chitos. DN = Chitosan-N-di-acetic acid nitrile
[7]yield related to moist product (FW), air-dried (except Example 8; dried at 60° C. in high vacuum)
[8]$CH_2O$, used as paraformaldehyde; total reaction at room temperature TABLE 2b Elemental analysis[9]

| Ex. | | | | | | | | | |
|---|---|---|---|---|---|---|---|---|---|
| 5 | $C_{calc}$ | 49.04 | $H_{calc}$ | 5.8 | $N_{calc}$ | 14.99 | $O_{calc}$ | 30.17 |
|  | $C_{found}$ | 49.44 | $H_{found}$ | 5.2 | $N_{found}$ | 14.76 | $O_{found}$ | 30.6 |
| 6 | $C_{calc}$ | 48.75 | $H_{calc}$ | 5.88 | $N_{calc}$ | 14.51 | $O_{calc}$ | 30.86 |
|  | $C_{found}$ | 49.08 | $H_{found}$ | 5.62 | $N_{found}$ | 14.36 | $O_{found}$ | 30.94 |
| 7 | $C_{calc}$ | 48.74 | $H_{calc}$ | 5.88 | $N_{calc}$ | 14.44 | $O_{calc}$ | 30.94 |
|  | $C_{found}$ | 49.37 | $H_{found}$ | 5.21 | $N_{found}$ | 14.13 | $O_{found}$ | 31.29 |
| 8 | $C_{calc}$ | 48.26 | $H_{calc}$ | 6.01 | $N_{calc}$ | 13.60 | $O_{calc}$ | 32.14 |
|  | $C_{found}$ | 48.51 | $H_{found}$ | 5.07 | $N_{found}$ | 13.503 | $O_{found}$ | 32.91 |
| 9 | $C_{calc}$ | 48.70 | $H_{calc}$ | 5.88 | $N_{calc}$ | 14.60 | $O_{calc}$ | 30.82 |
|  | $C_{found}$ | 48.87 | $H_{found}$ | 5.17 | $N_{found}$ | 14.54 | $O_{found}$ | 31.42 |
| 10 | $C_{calc}$ | 48.81 | $H_{calc}$ | 5.86 | $N_{calc}$ | 14.77 | $O_{calc}$ | 30.57 |
|  | $C_{found}$ | 48.92 | $H_{found}$ | 5.23 | $N_{found}$ | 14.99 | $O_{found}$ | 31.36 |
| 11 | $C_{calc}$ | 48.84 |  | 5.85 | $N_{calc}$ | 14.83 | $O_{calc}$ | 30.49 |
|  | $C_{found}$ | 49.03 |  | 5.03 | $N_{found}$ | 14.40 | $O_{found}$ | 31.54 |

[9]determination of water content: $H_2O$ expelled at 130° C. (K: Fischer)

The reaction was carried out in the following manner:

NaCN in solid form is slowly charged into the formic acid solution of the partial deacetylated chitin (C1–C4) at a temperature of 0° to 5° C. The first half of the formaldehyde, preferably as 37% by weight solution of formaline or paraformaldehyde is added at the same temperature. Then the temperature is raised to 40° C. (respectively 60° C.), and the second half of the formaldehyde is added. After reaction the product solution which is mostly coloured blue-green is charged into a sufficient water. The polymeric nitrile ("chitosan"-N-(di)-acetic acid nitrile) is practically completely water insoluble from a substitution degree of 50% and can be isolated quantitatively as blue-grey, gum-like, viscous mass. The ratio precipitation bath/reaction solution is 5:1. The polymeric material is crushed in a mixer in the presence of water, the suspension is neutralised with NaOH, the material which still contains encluded formic acid, is isolated by suction filtration, after washed and air-dried (=moist product). For hydrolysis the material is used in this soaking state.

A sample of c. 10 g is weighed exactly and dried at 60° C. for 24 hours in high vacuum.

The simplified calculation of the substitution degree (DS) reveres to a terpolymer having the units Chitin (moiety of the starting material, which remains unchanged under the reaction conditions), chitosan and chitosan-N-acetic acid nitrile.

EXAMPLES 12 to 18

The chitosan-N-acetic acid nitriles obtained in the Examples 5 to 11 are suspended as moist product for hydrolysis in c. 1,5% of NaOH and overboiled at 80° C. for sufficient time. The obtained bright-yellow aqueous solutions are clarified in a G 2 filter gauze and reduced at a rotation flask at 60°–70° C. (jet-water vacuum). The high viscous solutions are then precipitated into 96% ethanol. The material isolated by suction filtration is dried at 50° C. in the dry oven at high vacuum in the presence of $CaCl_2$ and then crushed in a mixer. aspect: bright-yellow, nearly colourless powder. The polymeric amino acid having the polysaccha-ride backbone contains Na-formiate as admixture, which is precipitated during precipitation into ethanol.

Reaction parameters and compositions of the hydrolysis products are listed In Table 3a.

TABLE 3a

| | | | | | | Composition | | | | | |
|---|---|---|---|---|---|---|---|---|---|---|---|
| Ex. | FW [g] | $H_2O$ deion. [ml] | NaOH [mol] | Reac. time [h] | yield[10] [g] [%] | (Chito-san)$_x$ x [mol] | (Chitos.-ND-Na)$_y$ y [mol] | (HCOONa)$_z$ z [mol] | MG [Da] | IEP[11] [pH] | $\eta_{red}$[12] [dl/g] [% G/V] |
| 12[13] | 157.53 | 650 | 0.364 | 38 | 27.21 93.1 | 0.3300 | 0.6700 | 0.7500 | 319.4 | 5.24 | 6.576 0.5009 |
| 13[14] | 190.02 | 650 | 0.330 | 72 | 25.32 85.8 | 0.3924 | 0.6076 | 0.8400 | 315.6 | 4.71 | 9.014 0.5020 |
| 14[15] | 208.86 | 650 | 0.329 | 48 | 26.58 96.4 | 0.3979 | 0.6021 | 0.5420 | 294.4 | 4.73 | 2.730 0.5007 |

TABLE 3a-continued

| | | | | | | Composition | | | | | |
|---|---|---|---|---|---|---|---|---|---|---|---|
| Ex. | FW [g] | H₂O deion. [ml] | NaOH [mol] | Reac. time [h] | yield[10] [g] [%] | (Chitosan)$_x$ x [mol] | (Chitos.-ND-Na)$_y$ y [mol] | (HCOONa)$_z$ z [mol] | MG [Da] | IEP[11] [pH] | $\eta_{red}$[12] [dl/g] [% G/V] |
| 15[16] | 20.42 | 830 | 0.295 | 96 | 22.23 74.1 | 0.5000 | 0.5000 | 1.0000 | 309.2 | 4.60 | 3.970 0.5008 |
| 16[17] | 494.70 | 2368 | 1.120 | 120 | 90.99 94.4 | 0.3930 | 0.6070 | 0.9190 | 320.8 | — | 6.861 0.5008 |
| 17[18] | 403.60 | 2224 | 1.028 | 120 | 88.9 98.9 | 0.3700 | 0.6300 | 0.9800 | 328.6 | — | 4.174 |
| 18[19] | 464.60 | 2268 | 1.069 | 120 | 87.6 92.8 | 0.3630 | 0.6370 | 1.0900 | 337.2 | — | 2.977 0.5013 |

[10]related to water-free product
[11]IEP = isoelectric point; determined alkalimetric (s. R.A.A. Muzzarelli et al., Carbohydrate Research) 107, 202, 207 and 208 (1982)
[12]reduced viscosity; metered with Ubbelohde-viscosity meter type I, 25° C., solutions of the listed concentration [% G/V] in deionised water
[13]chitosan-N-acetic acid nitrile form Example 5
[14]chitosan-N-acetic acid nitrile form Example 6
[15]chitosan-N-acetic acid nitrile form Example 7
[16]chitosan-N-acetic acid nitrile form Example 8
[17]chitosan-N-acetic acid nitrile form Example 9
[18]chitosan-N-acetic acid nitrile form Example 10
[19]chitosan-N-acetic acid nitrile form Example 11

TABELLE 3b

Elemental analysis[20]

| Ex. | | | | | | | | | | | |
|---|---|---|---|---|---|---|---|---|---|---|---|
| 12 | $C_{calc}$ | 35.46 | $H_{calc}$ | 4.13 | $N_{calc}$ | 4.39 | $O_{calc}$ | 40.98 | $Na_{calc}$ | 15.04 |
| | $C_{found}$ | 34.25 | $H_{found}$ | 4.07 | $N_{found}$ | 4.28 | $O_{found}$ | 42.35 | $Na_{found}$ | 15.05 |
| 13 | $C_{calc}$ | 35.29 | $H_{calc}$ | 4.17 | $N_{calc}$ | 4.44 | $O_{calc}$ | 41.13 | $Na_{calc}$ | 14.97 |
| | $C_{found}$ | 33.61 | $H_{found}$ | 4.00 | $N_{found}$ | 4.20 | $O_{found}$ | 43.26 | $Na_{found}$ | 14.93 |
| 14 | $C_{calc}$ | 36.52 | $H_{calc}$ | 4.36 | $N_{calc}$ | 4.76 | $O_{calc}$ | 40.72 | $Na_{calc}$ | 13.64 |
| | $C_{found}$ | 36.74 | $H_{found}$ | 4.71 | $N_{found}$ | 4.16 | $O_{found}$ | 40.73 | $Na_{found}$ | 13.68 |
| 15 | $C_{calc}$ | 34.96 | $H_{calc}$ | 4.24 | $N_{calc}$ | 4.53 | $O_{calc}$ | 41.40 | $Na_{calc}$ | 14.87 |
| | $C_{found}$ | 34.48 | $H_{found}$ | 4.05 | $N_{found}$ | 4.41 | $O_{found}$ | 42.25 | $Na_{found}$ | 14.81 |
| 16 | $C_{calc}$ | 34.99 | $H_{calc}$ | 4.13 | $N_{calc}$ | 4.37 | $O_{calc}$ | 41.23 | $Na_{calc}$ | 15.29 |
| | $C_{found}$ | 33.89 | $H_{found}$ | 4.81 | $N_{found}$ | 3.68 | $O_{found}$ | 42.82 | $Na_{found}$ | 14.80 |
| 17 | $C_{calc}$ | 34.72 | $H_{calc}$ | 4.06 | $N_{calc}$ | 4.26 | $O_{calc}$ | 41.26 | $Na_{calc}$ | 15.67 |
| | $C_{found}$ | 33.90 | $H_{found}$ | 4.69 | $N_{found}$ | 3.79 | $O_{found}$ | 42.60 | $Na_{found}$ | 15.02 |
| 18 | $C_{calc}$ | 34.33 | | 4.00 | $N_{calc}$ | 4.15 | $O_{calc}$ | 41.41 | $Na_{calc}$ | 16.12 |
| | $C_{found}$ | 33.07 | | 4.36 | $N_{found}$ | 3.55 | $O_{found}$ | 42.94 | $Na_{found}$ | 16.08 |

[20]determination of water content: H₂O expelled at 130° C. (K: Fischer)

EXAMPLE 19

Determination of capacity for complexing metal ions of the polysaccharide-polyamino carbonic acids

TABLE 4

| polysaccha-ride-polyamino carbonic acid from Ex. | $Fe^{3+}$ [mg/g]: pH 6 | $Ni^{2+}$ [mg/g]: pH 6 | $Cd^{2+}$ [mg/g]: pH 6 | $Mn^{2+}$ [mg/g]: pH 6 | $Ca^{2+}$ [mg/g]: pH 9.5 |
|---|---|---|---|---|---|
| 12 | 117 | 52 | 109 | 76 | 65 |
| 13 | 134 | 66 | 118 | 69 | 63 |
| 14 | 125 | 50 | 104 | 66 | 67 |
| 15 | 132 | 57 | 110 | 68 | 66 |
| 16 | 122 | 80 | 99 | 93 | 96 |
| 17 | 113 | 75 | 89 | 80 | 88 |
| 18 | 136 | 69 | 101 | 95 | 85 |

EXAMPLE 20

Use in cosmetics
Preparation of a sun protective cream

| | |
|---|---|
| 7.5 pts octylmethoxyzinnamate | 1.0 pt PEG-40 stearate |
| 5 pts octyl salicylate | 1.0 pt methicon |
| 5 pts methyl anthranilate | 0.75 pt cetyl alcohol |
| 2 pts isocetyl alcohol | 0.25 pt toceropheryl acetate and |
| 2 pts cetearyl alcohol | 6 pt zinc oxide |
| 1.5 pts glyceryl stearate | | are mixed and the mixture is heated to 75°–80° C. Then 0.5 part of magnesium aluminium silicate is dispersed in 63.8 parts of water with a commercially available ball, vibration or hammer mill. To the dispersion is then added 0.5 part of xanthane gum and the batch is stirred until a homogeneous solution forms. The batch is then heated to 75°–80° C. while adding 0.2 part of the compound prepared in Example 4. To this solution is then added, with stirring, the compounds initially mixed and heated to 75°–80° C. After grinding for 10–15 minutes, the mixture is cooled to 40° C. and 1 part of propylene glycol is added. With further stirring, the composition is cooled to room temperature.

The composition is suitable for use as moisturising sun protective cream.

What is claimed is:

1. A N-cyanomethylated chitosan containing repeating units of formula

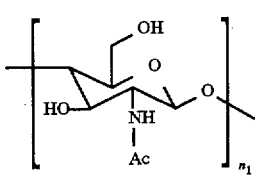

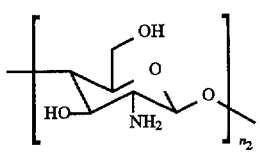

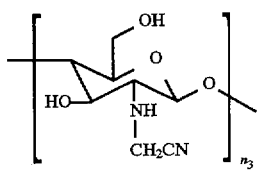

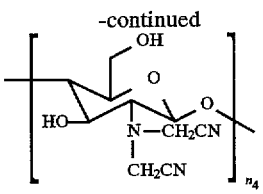

wherein
$n_1$ is 0 to 0.6
$n_2$ is 0 to 0.20
$(n_3+n_4)$ is 0.4 to 1.0.

2. A process for the preparation of a N-cyanomethylated chitosan according to claim 1, which comprises reacting chitosan with formaldehyde and hydrogen cyanide in the temperature range from 10° to 70° C. and in a reaction time of 0.5 to 12 hours in accordance with the following reaction scheme:

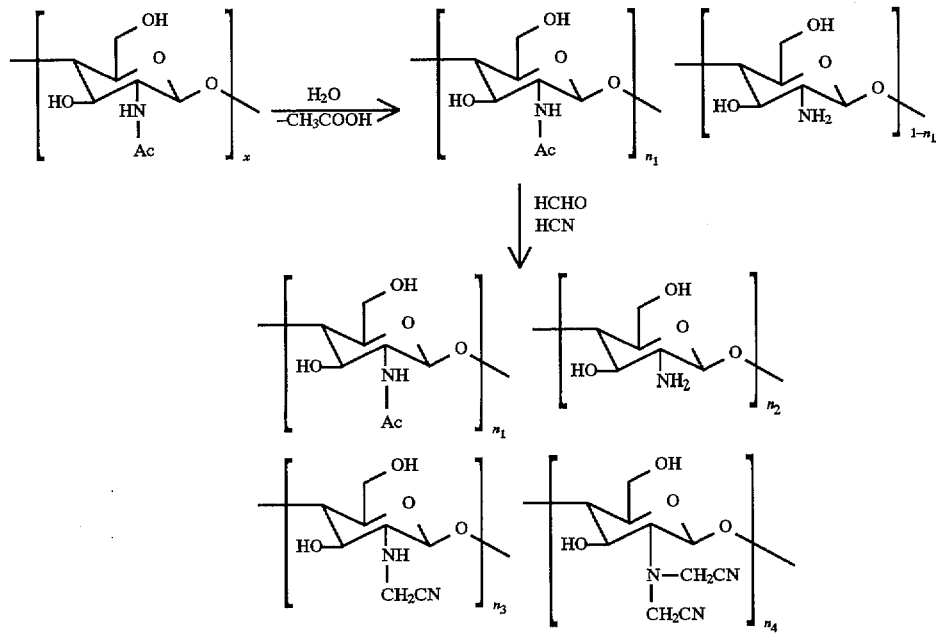

wherein
x is 5 to 10 000
$n_1$ is 0 to 0.6 part, based on x;
$n_2$ is 0 to 0.2 part, based on x;
$(n_3+n_4)$ is 0.4 to 1.0 part, based on x.

3. A process according to claim 2, wherein the reaction is carried out in the presence of formic acid.

4. A N-cyanomethylated chitosan according to claim 1, wherein $n_1$ is 0.05 to 0.20;
$n_2$ is 0.05 to 0.10; and
$(n_3+n_4)$ is 0.8 to 0.95.

5. A process according to claim 2 having a reaction time of from 2 to 5 hours.

6. A process according to claim 2, wherein
x is 20 to 500;
$n_1$ is 0.05 to 0.2, based on x;
$n_2$ is 0.05 to 0.1, based on x; and
$(n_3+n_4)$ is 0.8 to 0.95 part, based on x.

* * * * *